(12) United States Patent
Heinonen

(10) Patent No.: US 9,539,406 B2
(45) Date of Patent: Jan. 10, 2017

(54) INTERFACE DEVICE AND METHOD FOR SUPPLYING GAS FLOW FOR SUBJECT BREATHING AND APPARATUS FOR SUPPLYING ANESTHETIC AGENT TO THE INTERFACE DEVICE

(71) Applicant: General Electric Company, Schenectady, NY (US)

(72) Inventor: Erkki Heinonen, Helsinki (FI)

(73) Assignee: General Electric Company, Schenectady, NY (US)

( * ) Notice: Subject to any disclaimer, the term of this patent is extended or adjusted under 35 U.S.C. 154(b) by 439 days.

(21) Appl. No.: 14/022,319

(22) Filed: Sep. 10, 2013

(65) Prior Publication Data

US 2015/0068520 A1    Mar. 12, 2015

(51) Int. Cl.
| | |
|---|---|
| *A61M 15/00* | (2006.01) |
| *A61M 16/00* | (2006.01) |
| *A61M 16/08* | (2006.01) |
| *A61M 16/10* | (2006.01) |
| *A61M 16/18* | (2006.01) |
| *A61M 16/01* | (2006.01) |

(Continued)

(52) U.S. Cl.
CPC ..... *A61M 16/0816* (2013.01); *A61M 16/0891* (2014.02); *A61M 16/104* (2013.01); *A61M 16/18* (2013.01); *A61M 16/202* (2014.02); *A61M 16/01* (2013.01); *A61M 16/12* (2013.01); *A61M 16/208* (2013.01); *A61M 16/22* (2013.01); *A61M 2202/0208* (2013.01); *A61M 2202/0266* (2013.01); *A61M 2202/0283* (2013.01)

(58) Field of Classification Search
CPC .. A61M 16/186; A61M 16/104; A61M 16/18; A61M 16/01; A61M 16/10; A61M 16/0816; A61M 16/12; A61M 16/20; A61M 16/122; A61M 16/125; A61M 16/201; A61M 16/202; Y10T 137/87113; Y10T 74/2025; Y10T 137/87048; Y10T 137/86879; Y10T 137/87249

USPC ..... 137/625.67, 625.69, 625.65, 625.48, 597
See application file for complete search history.

(56) References Cited

U.S. PATENT DOCUMENTS

| | | | | |
|---|---|---|---|---|
| 1,613,150 A | * | 1/1927 | Zore | G01M 3/2846 137/199 |
| 2,045,823 A | * | 6/1936 | Barrow | F24D 19/1024 122/20 A |

(Continued)

*Primary Examiner* — Bradley Philips
*Assistant Examiner* — Victoria Leszczak
(74) *Attorney, Agent, or Firm* — Andrus Intellectual Property Law, LLP

(57) ABSTRACT

An interface device for supplying a gas flow for breathing is disclosed herein. The device includes at least one socket for detachably connecting an apparatus for supplying anesthetic agent, at least one gas output opening for delivering the fresh gas to the apparatus, and at least one gas input opening for receiving the fresh gas mixed with anesthetic agent. The device also includes a connection valve and at least four ports in flow communication with the valve, a first port receiving the gas, a second port providing a communication with the output opening, a third port providing a communication with the input opening, and a fourth port providing a communication for breathing, the valve having a first operational state disconnecting communication between the first and second port, and to second operational state providing communication between the first and second port, but also between the third and fourth port.

16 Claims, 3 Drawing Sheets

(51) Int. Cl.
  *A61M 16/12* (2006.01)
  *A61M 16/20* (2006.01)
  *A61M 16/22* (2006.01)

(56) References Cited

U.S. PATENT DOCUMENTS

| | | | | |
|---|---|---|---|---|
| 2,182,982 A * | 12/1939 | Evans | ............... | F15B 13/04 137/625.48 |
| 2,206,163 A * | 7/1940 | Shakespeare | ......... | B64C 25/22 137/637.1 |
| 2,214,119 A * | 9/1940 | Brisbane | ............... | F16K 31/36 137/512 |
| 2,354,694 A * | 8/1944 | McGill | ............... | C02F 1/42 137/552 |
| 2,636,566 A * | 4/1953 | Jedrziewski | ......... | B64C 11/303 137/54 |
| 2,719,518 A * | 10/1955 | Newman | ............... | F02M 13/08 123/557 |
| 3,033,196 A * | 5/1962 | Hay | ............... | A61M 16/00 128/204.25 |
| 3,109,442 A * | 11/1963 | Horowitz | ............ | B60T 11/326 137/111 |
| 3,139,908 A * | 7/1964 | Strader | ............... | F16D 25/14 137/625.48 |
| 3,251,359 A * | 5/1966 | Ismach | ............... | A61M 16/00 128/205.16 |
| 3,308,851 A * | 3/1967 | Zoludow | ............... | F16K 11/0716 137/102 |
| 3,331,368 A * | 7/1967 | Bird | ............... | A61M 16/00 128/205.24 |
| 3,502,099 A * | 3/1970 | Wilson | ............... | A61M 16/20 137/102 |
| 3,662,751 A * | 5/1972 | Barkalow | ............ | A61M 16/00 128/204.25 |
| 3,727,627 A * | 4/1973 | Bird | ............... | A61M 16/12 128/205.11 |
| 3,776,276 A * | 12/1973 | Stiltner | ............... | F16K 11/0655 137/625.18 |
| 3,955,597 A * | 5/1976 | Oneyama | ............ | F15B 13/0405 137/625.25 |
| 3,973,583 A * | 8/1976 | Sorenson | ............ | F15B 13/0402 137/312 |
| 3,974,828 A * | 8/1976 | Bird | ............... | A61M 16/00 128/204.25 |
| 3,990,553 A * | 11/1976 | Holzinger | ............ | F16H 61/0272 192/109 F |
| 4,058,120 A * | 11/1977 | Caparrelli | ............ | A61M 16/186 128/203.12 |
| 4,061,160 A * | 12/1977 | Kashmer | ............ | A61M 16/104 128/205.24 |
| 4,202,330 A * | 5/1980 | Jariabka | ............... | A61M 16/20 128/204.18 |
| 4,253,453 A * | 3/1981 | Hay | ............... | A61M 16/186 128/200.19 |
| 4,346,701 A | 8/1982 | Richards | | |
| 4,422,475 A * | 12/1983 | Aspinwall | ......... | F15B 13/0402 137/596.17 |
| 4,471,775 A * | 9/1984 | Clair | ............... | A61M 16/044 128/205.24 |
| 4,579,143 A * | 4/1986 | Rollins | ............... | F23K 5/147 137/238 |
| 4,770,168 A * | 9/1988 | Rusz | ............... | A61M 16/18 128/203.12 |
| 5,236,015 A * | 8/1993 | Schwelm | ............... | F15B 13/043 137/625.18 |
| 5,337,738 A * | 8/1994 | Heinonen | ............ | A61M 16/18 128/203.12 |
| 5,520,170 A * | 5/1996 | Laswick | ............ | A61M 16/20 128/204.18 |
| 5,537,992 A * | 7/1996 | Bjoernstijerna | .. | A61M 16/1015 128/200.19 |
| 5,666,945 A * | 9/1997 | Davenport | ............ | A61M 16/20 128/200.14 |
| 5,797,389 A * | 8/1998 | Ryder | ............... | A61M 11/06 128/200.21 |
| 5,806,513 A * | 9/1998 | Tham | ............... | A61M 16/104 128/203.12 |
| 5,824,885 A * | 10/1998 | Lekholm | ............ | A61M 16/209 128/203.12 |
| 5,836,302 A * | 11/1998 | Homuth | ............ | A61M 16/0051 116/142 FP |
| 5,921,235 A * | 7/1999 | Kronekvist | ......... | A61M 16/186 128/203.12 |
| 6,024,087 A * | 2/2000 | Kersey | ............... | A61M 16/12 128/203.12 |
| 6,615,831 B1 * | 9/2003 | Tuitt | ............... | A61M 16/08 128/204.18 |
| 7,134,434 B2 * | 11/2006 | Truitt | ............... | A61M 16/08 128/200.24 |
| 2001/0035220 A1 * | 11/2001 | Russell | ............... | E21B 21/106 137/625.48 |
| 2003/0034076 A1 * | 2/2003 | Kim | ............... | F16K 11/07 137/625.48 |
| 2003/0127098 A1 * | 7/2003 | Fjeld | ............... | A61M 16/20 128/204.26 |
| 2003/0131849 A1 * | 7/2003 | Figley | ............... | A61M 16/00 128/204.18 |
| 2004/0144385 A1 * | 7/2004 | Bromster | ............ | A61M 16/08 128/205.13 |
| 2006/0202067 A1 * | 9/2006 | Mitsui | ............... | B05B 5/1608 239/690.1 |
| 2007/0277824 A1 * | 12/2007 | Aylsworth | ......... | A61M 16/0666 128/204.23 |
| 2008/0115787 A1 * | 5/2008 | Ingenito | ............... | A61M 11/008 128/205.13 |
| 2009/0179157 A1 * | 7/2009 | Sinclair | ............... | C23C 14/228 250/423 R |
| 2011/0100362 A1 * | 5/2011 | Baecke | ............... | A61M 16/12 128/203.12 |
| 2014/0366874 A1 * | 12/2014 | Deutsch | ............ | A61M 16/044 128/202.13 |
| 2015/0144215 A1 * | 5/2015 | Bellofatto | ............ | A61B 1/015 137/625.69 |
| 2016/0001033 A1 * | 1/2016 | Van De Ven | ......... | F16K 27/04 128/205.24 |

\* cited by examiner ized for patient breathing in anesthesia vaporizer. The most common inhalation anesthesia drugs are isoflurane, sevoflurane and desflurane. These have replaced the use of their predecessors, halothane and enflurane.
INTERFACE DEVICE AND METHOD FOR SUPPLYING GAS FLOW FOR SUBJECT BREATHING AND APPARATUS FOR SUPPLYING ANESTHETIC AGENT TO THE INTERFACE DEVICE

BACKGROUND OF THE INVENTION

This disclosure relates generally to an interface device and method for supplying gas flow for subject breathing. The disclosure also relates to an apparatus for supplying anesthetic agent to the interface device.

On general inhalation anesthesia anesthetic drugs are used to keep patients experiencing surgical operation relaxed, motionless, unconscious, and free from pain. The anesthetic drugs interfere on the central nervous system for these effects. On inhalation anesthesia the anesthetic drugs are delivered with breathing gas to lungs where they get diffused to patient blood circulation. This circulation further carries the drug to the effect site in brains.

Inhalation anesthesia drugs are halogenated hydrocarbons that are delivered on administration site as liquids. These liquids are very volatile with vapor pressure at room temperature varying between 20-95 kPa. These liquids are vaporized for patient breathing in anesthesia vaporizer. The most common inhalation anesthesia drugs are isoflurane, sevoflurane and desflurane. These have replaced the use of their predecessors, halothane and enflurane.

For various reasons preference of the agent to be used varies between patients and clinics. Conventional vaporizers are heavy devices to enclose thermal energy for the cooling caused by liquid vaporization. The devices are positioned for convenient use of the output concentration dial embedded on the device. Because of the weight and elevated position at anesthesia system, their installation may be laborious for clinical personnel. For this reason the anesthesia machines are equipped with functionality that enables easy selection of the agent to be used among those readily connected to the system. Anesthesia system accommodates therefore often two or three sockets to connect the vaporizer. Advantage of separate, anesthesia system independent module for vaporization provides is to have functional redundancy against vaporizer failure.

In operation, vaporizer receives fresh gas, which is a mixture of oxygen, nitrogen, and nitrous oxide, and completes that with required percentage of the anesthetic drug vapor. On conventional passive vaporizers the completion occurs with vaporization of the liquid agent respective to its vapor pressure. Alternate technologies are active vaporization of liquid to gas and control of this gas flow, or controlling agent liquid flow and mixing to fresh gas stream. The prepared fresh gas is then delivered from vaporizer outlet to anesthesia breathing system for patient.

Arising from the operational principle of vaporizers, if two vaporizers would be active in anesthesia system they would both deliver the required concentration to the gas stream. Both of these drugs would then get delivered for patient breathing and circulation to effect-site both drug causing their effect resulting to doubled strength of the anesthesia effect. Clinically such situation is challenging to manage and may be dangerous. Therefore vaporizer constructional standards require mechanisms that prevents simultaneous opening of the vaporizers.

In vaporizer failure situation for provision of un-interrupted inhalation anesthesia delivery, the anesthesia system must have means to isolate the failing vaporizer from the pneumatic circuitry and continue the anesthesia with another vaporizer connected to the anesthesia system, or replace the damaged unit with an operational one. To achieve isolation, the components potentially endangered to fail are advantageously positioned to the exchangeable module and the anesthesia system has reliable means to isolate the vaporizer from the rest of the system. Isolating the vaporizer from anesthesia system pneumatic circuitry when the vaporizer is inactive also ensures that vaporizer not selected for use does not leak vapor for patient breathing. Current anesthesia systems have a valve at the vaporizer inlet connector and outlet connector. These valves can be switched to position allowing gas flow through vaporizer or bypassing the vaporizer.

One of the most sensitive components that renders a vaporizer unusable is a leak of the seal between the vaporizer and the anesthesia system. Damage may occur when removing and installing the vaporizer on the anesthesia system. Identifying the presence of such a leak is difficult in the middle of delivering anesthesia. Therefore the vaporizer connection is advantageously evaluated at the anesthesia system testing performed regularly. In such testing, identification of the site for observed leak is advantageous to ease problem solving. Valves on the anesthesia system isolating the seal between the vaporizer and anesthesia system provides advantage of controlled testing of the leak in this connection. In such testing, one vaporizer at a time is connected to the pneumatic circuitry and the circuit leak is analyzed by pressurizing the circuit.

One particular undesired failure mode of anesthesia system is occlusion of the fresh gas line. When in use fresh gas is guided to the vaporizer though an inlet valve and out from the vaporizer through an outlet valve. When one of the valves makes a proper connection, but the other fails to make the connection, fresh gas occlusion occurs. Such a failure to open one of the valves may occur if that valve gets stuck or the valve actuator is broken.

Modern anesthesia systems are electronic other than vaporizers, where the mechanical actuation (including connection valves) and passive vaporization still dominate. These devices lack what electronics provide, such as automatic therapy data storage to patient records, automated device diagnostics, drug usage measurement, monitoring remaining drug level and external control of the desired output from anesthesia system.

However, external electronic control of the vaporizer from anesthesia system allows positioning of the vaporizers away from the prime user interface area, as well as providing anesthesia automation. Provision of electrical energy for vaporization miniaturizes size and weight, enabling ergonomic development of anesthesia systems. Such electronically controlled vaporizers must also have electronic control of the vaporizer connection valves to facilitate automatic vaporizer activation on user request for agent output and for automatic testing.

BRIEF DESCRIPTION OF THE INVENTION

The above-mentioned shortcomings, disadvantages and problems are addressed herein which will be understood by reading and understanding the following specification.

In an embodiment an interface device for supplying a gas flow for subject breathing includes at least one socket for detachably connecting an apparatus for supplying anesthetic agent, and at least one gas output opening for the at least one socket for delivering the fresh gas to the apparatus. The interface device also includes at least one gas input opening for the at least one socket for receiving from the apparatus the fresh gas mixed with anesthetic agent to supply further for subject breathing, and a connection valve for the at least one socket. The interface device also includes at least four ports in flow communication with the connection valve, a first port receiving the fresh gas guided to the device, a second port providing a gas flow communication with the at least one gas output opening, a third port providing a gas flow communication with the at least one gas input opening, and a fourth port providing a gas flow communication for subject breathing, the connection valve having a first operational state disconnecting a gas flow communication between the first port and the second port, and a second operational state providing a gas flow communication besides between the first port and the second port, but also between the third port and the fourth port.

In another embodiment an apparatus for supplying anesthetic agent to an interface device, the device being configured to receive a fresh gas flow and to provide the gas flow for subject breathing, the apparatus being configured to connect detachably with the interface device, the apparatus includes a storage volume for a liquid anesthetic agent, and a space for vaporizing the liquid anesthetic agent. The apparatus also includes a gas inlet port for receiving from the device a fresh gas for mixing with vaporized anesthetic agent, and a gas outlet port for conducting the gas mixture including vaporized anesthetic agent out from the space to the interface device. The apparatus also includes an actuator for connecting the fresh gas flow through the gas inlet port and the gas outlet port and disconnecting this flow when required, the actuator being able to provide a control of the fresh gas flow through the gas inlet port and the gas outlet port by means of a single communication member extending between the apparatus and the interface device.

In yet another embodiment a method for supplying the gas flow from an interface device for subject breathing includes connecting detachably an apparatus for supplying anesthetic agent to at least one socket of the interface device, and delivering a fresh gas through at least one gas output opening of the at least one socket to the apparatus. The method also includes receiving through at least one input opening of the at least one socket from the apparatus the fresh gas mixed with anesthetic agent to provide further for subject breathing, and providing gas flow communication in the interface device between a connection valve and at least four ports, a first port receiving the fresh gas guided to the device, a second port providing a gas flow communication with the at least one gas output opening, a third port providing a gas flow communication with the at least one gas input opening, and a fourth port providing a gas flow communication for subject breathing, the connection valve having a first operational state disconnecting a gas flow communication between the first port and the second port, and a second operational state providing a gas flow communication besides between the first port and the second port, but also between the third port and the fourth port.

Various other features, objects, and advantages of the invention will be made apparent to those skilled in the art from the accompanying drawings and detailed description thereof.

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 1:
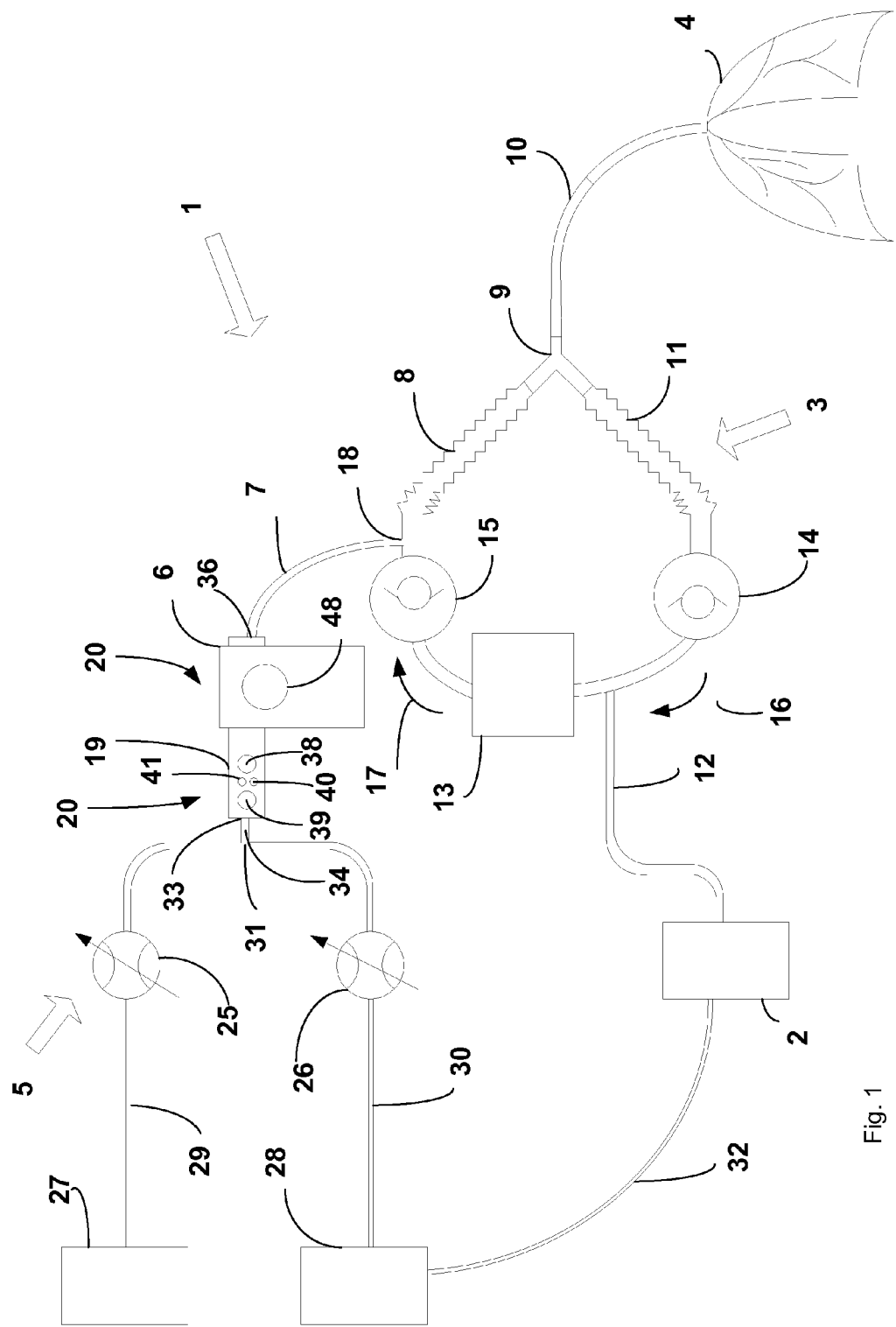
FIG. 1 illustrates an operational diagram of an anesthesia system comprising an interface device for supplying gas flow and an apparatus for supplying anesthetic agent for subject breathing in accordance with an embodiment.

An anesthesia system 1 for supplying an inspiration gas to lungs of a subject shown in FIG. 1 may comprise a ventilator 2 for assisting breathing function of the subject, a breathing circuit 3 for connecting lungs 4 of the subject and the ventilator 2, a fresh gas mixer 5 for preparation of the appropriate breathing gas mixture of oxygen and nitrogen or nitrous oxide and to control its flow rate, and the apparatus 6 such as a vaporizer for supplying anesthetic agent to the fresh gas mixture received from the fresh gas mixer and which anesthetic agent mixed with the fresh gas mixture is supplied to the breathing circuit. The apparatus 6 is able to add anesthetic agent in user dialed concentration to the fresh gas flow. The apparatus comprises a user interface 48, such as a dial for providing a signal indicative of a concentration setting. The anesthesia system 1 can accommodate one or more apparatus. The complete fresh gas mixture is conducted from the fresh gas mixer 5 and the apparatus 6 to the breathing circuit 3 through the fresh gas line 7.

In the breathing circuit 3 the fresh gas coming from the fresh gas mixer 5 and the apparatus 6 through a fresh gas outlet 18 is mixed with the re-circulated breathing gas at the circuit. During inspiration this mixture is guided through an inspiration line 8 to a branching unit 9 and further through a connection line 10 to a subject's lungs 4, causing them to expand. Expiration follows inspiration when the drive of the breathing gases into the lung is ceased. At this moment the compliant forces of the lungs pressurize the gas in the lungs. Expiration flow begins when the ventilator 2 opens an expiration control valve within the ventilator (not shown). Pressurized gas from the lungs 4 flows out through the connection line 10 to the branching unit 9 and further through an expiration line 11 to a ventilator limb 12 and to the ventilator 2. Within the ventilator the exhalation gas is advantageously at least partially preserved for the next inspiration. At the time of the next inspiration, the expiration control valve of the ventilator 2 is closed, the inspiration control valve of the ventilator (not shown) is opened to drive at least partly the previously exhaled breathing gas from the ventilator 2 back to the breathing circuit 3. Now the inspiration gas flows through a carbon dioxide (CO2) absorber 13 to remove the patient exhaled carbon dioxide before getting inhaled again and through the inspiration line 8 where the fresh gas is added along a fresh gas line 7. An expiration valve 14 and inspiration valve 15 guide the direction of rotation of the ventilation within the breathing circuit as indicated by arrows 16 and 17. The fresh gas outlet 18 may be upstream to the inspiration line, but the fresh gas outlet can be either downstream the inspiration valve 15 as presented or upstream.

The anesthesia system also includes an interface device 19 to supply the gas flow for subject breathing and to connect the apparatus 6 for supplying anesthetic agent to this interface device. The interface device 19 receiving fresh gas from the gas mixer 5 may comprise at least two sockets 20, each socket being for separate apparatus 6. Typically there is one socket for each apparatus for supplying anesthetic agent. The number of sockets is two in FIG. 1 accommodating maximum two apparatus the other socket being empty when only one apparatus module is connected, but naturally there can be more than that depending on the number of sockets in the interface device 19.

FIG. 1 shows the gas mixer for two gas channels both having control valve and measurement unit 25 and 26. The fresh gas is a mixture of oxygen, nitrogen and nitrous oxide. The gases are coming from pressurized gas supply 27 and 28 through lines 29 and 30. In FIG. 1 the pressure gas supply 27 is a source for oxygen and the pressure gas supply 27 is for air, which is typically a mixture of nitrogen and oxygen. Metered gas flows are mixed together at connection point 31 and directed to an interface inlet 33 through a gas line 34. From the interface device 19 the gas completed with requested concentration of anesthesia drug is guided from interface outlet 36 through the fresh gas line 7 to breathing circuit 3.

The ventilator 2 may be of any type common for anesthesia ventilation. These include pressure driven ventilators where the ventilator is powered using the supply pressure guided from pressurized gas supply 28 through a line 32 as presented on FIG. 1. The ventilator may be also electrically powered when the breathing circuit gas flow is induced using some electrically driven actuator.

Figure 4:
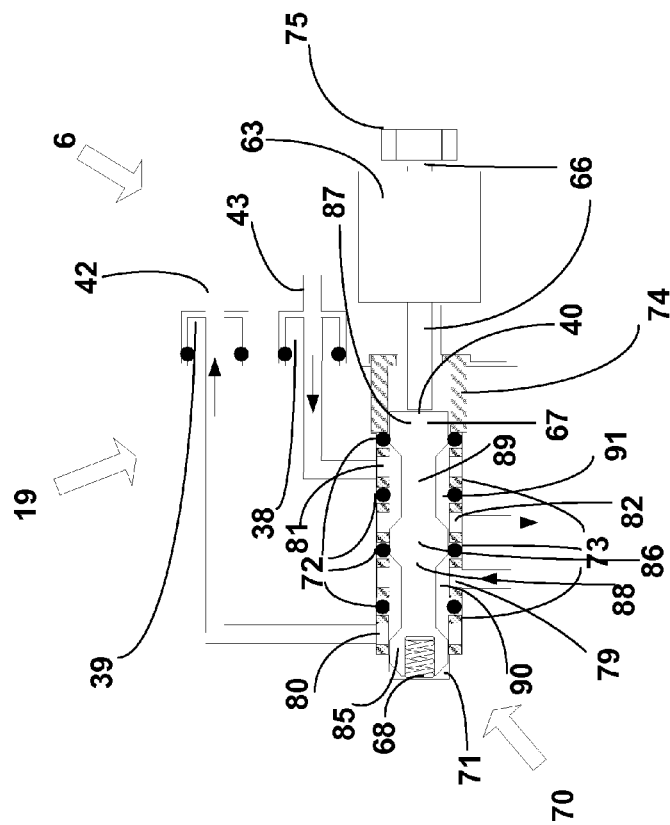
FIG. 4 illustrates a connection valve of the interface device in an operational state where anesthetic agent supply from the apparatus of FIG. 2 to the anesthesia system is connected.
Figure 3:
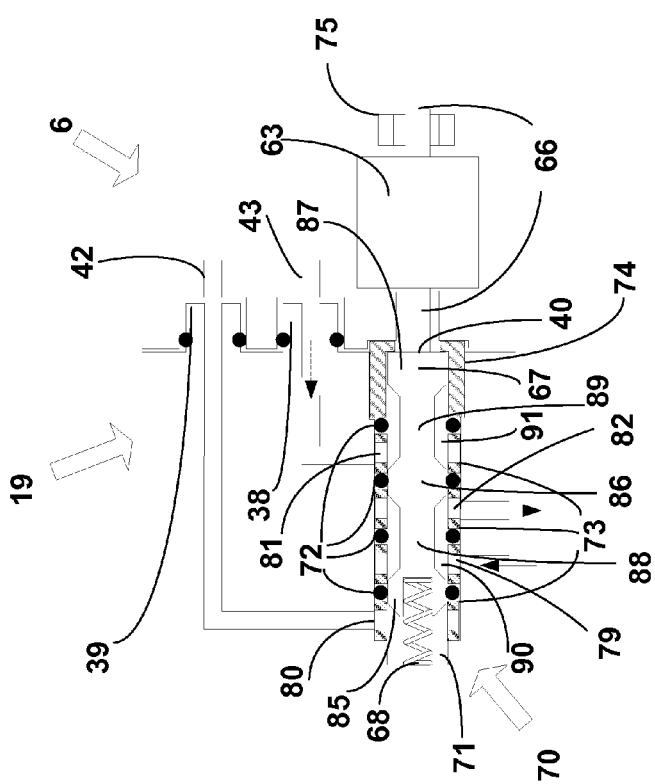
FIG. 3 illustrates a connection valve of the interface device in an operational state where anesthetic agent supply from the apparatus of FIG. 2 to the anesthesia system is disconnected.

Each socket of the interface device 19 may comprise at least one gas input opening 38 to receive the gas flow from the apparatus 6 for supplying anesthetic agent to the interface device and at least one gas output opening 39 to allow the gas flow from the interface device to the apparatus 6 for supplying anesthetic agent. The interface device 19 provides for each socket 20 also a connection valve interface 40 for communication with a connection valve 70 in the interface device 19 as shown in FIGS. 3 and 4. This connection valve, in its first operational state, such as in an inactive state, as shown in FIG. 3 disconnects a gas flow communication between the apparatus 6 and the interface device 19 and thus guide the fresh gas flow to pass the apparatus 6, and on its second operational state, such as in an active state, as shown in FIG. 4 provides a gas flow communication between the apparatus and the interface device and thus guide the fresh gas flow to the apparatus 6 through the at least one gas output opening 39 and receive the flow completed with requested amount of anesthesia agent vapor from apparatus 6 through the at least one gas input opening 38.

Figure 2:
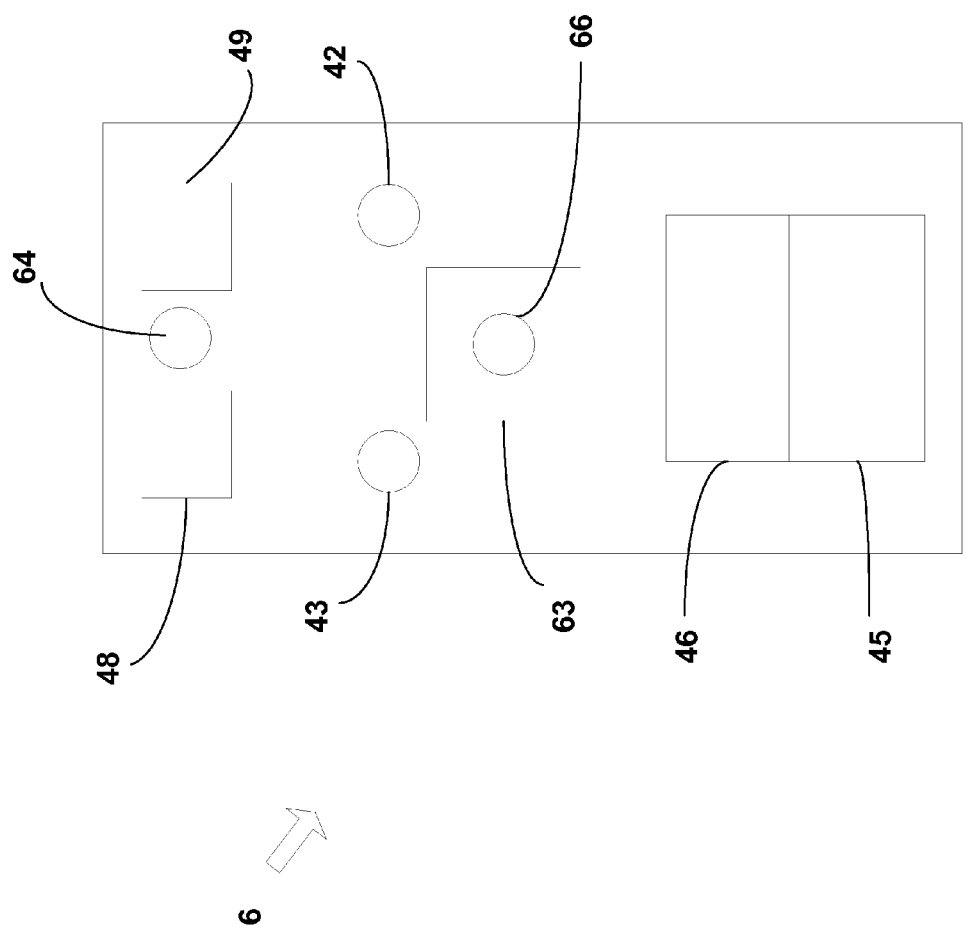
FIG. 2 illustrates the apparatus for supplying anesthetic agent in accordance with an embodiment.

A schematic view of the apparatus 6 for supplying anesthetic agent vapor to breathing gas for subject breathing is shown in FIG. 2. The apparatus 6 is a module detachable from the anesthesia system 1 and again re-mountable. Accordingly it can be said that the anesthesia system may connect detachably with at least two such apparatuses. The apparatus 6 may comprise at least one inlet port 42 for the fresh gas received from the gas output opening 39 of the interface device, which inlet port is in flow communication with the gas line 34, and at least one outlet port 43 for delivering vaporized anesthetic agent typically mixed with the fresh gas to the gas input opening 38 of the interface device 19 and which outlet port 43 is in flow communication with the fresh gas line 7 shown in FIG. 1. The apparatus 6 may also comprise a storage volume 45 for a liquid anesthetic agent. The liquid anesthetic agent originated in the storage volume 45 can be vaporized to a space 46 for vaporizing a liquid anesthetic agent which space is also part of the apparatus 6. The gas coming from the gas inlet port 42 is guided through the space 46 to mix it with the anesthetic agent vaporized. The mixture is guided to the gas outlet port 43 of the apparatus 6 for further delivering along the fresh gas line 7 to the breathing circuit 3 as shown in FIG. 1 for the subject breathing. The apparatus comprises also an actuator 63 that communicates through its communication member 66 with connection valve interface 40 in the interface device and finally with the connection valve 70. The actuator may connect the fresh gas flow through the gas inlet port and the gas outlet port and disconnect this flow when this is required.

The apparatus 6 may also comprise as explained hereinbefore a user interface 48, such as a dial, for entering a desired targeted amount of anesthetic agent to be outputted. The user interface may also be common with other parts of the anesthesia system 1 and need not be in the apparatus 6 module. Apparatus 6 may have a communication connection 64 to communicate via corresponding connection 41 on the interface 19 of the anesthesia system 1. The connection between the apparatus 6 and the anesthesia system 1 may be also wireless without physical connections. Further the apparatus 6 may comprise a logic circuit 49, such as a processing unit, to control the actuator 63 shown in FIGS. 2, 3 and 4. in the embodiment shown, the actuator is positioned in the apparatus. This enables continuation of inhalation anesthesia even when the actuator fails to operate the connection valve by changing the failed apparatus 6 to an operational one. This also allows inactivation of the connection valve by removing the apparatus in case the actuator fails to switch to inactive state. When being able to inactivate connection of failed apparatus, another apparatus 6 connected to the anesthesia system can be safely used. The actuator 63 of the connection valve 70 is controlled from a distance. For this purpose the actuator is controlled advantageously electrically. This enables automatic connection of the apparatus 6 to the anesthesia system when user begins anesthesia delivery and also automatic testing of the operational condition of the apparatus 6 and its connections as a part of anesthesia system testing. The activation of the apparatus 6 and delivery control from distance also enables positioning of one or more apparatus away from the prime user interface area when they do not request any more regular reach from the user.

A detailed connection between the components of the interface device 19 and the components of the apparatus 6 is shown in FIG. 3. The interface device 19 as explained hereinbefore comprises at least one gas input opening 38 and at least one gas output opening 39 in communication with the respective at least one outlet port 43 and at least one inlet port 42 of the apparatus 6 when the apparatus is connected to the interface device. At this moment also the communication member 66 of the actuator 63 gets ready for communication with the connection valve interface 40 and the valve member 67 of the connection valve 70.

The interface device 19 also comprises at least four ports in flow communication with the connection valve. A first port 79 is for receiving the fresh gas flow guided to the interface device through the interface inlet 33 to the connection valve 70, a second port 80 is for providing a gas flow communication from the connection valve 70 to the at least one gas output opening 39, a third port 81 is for providing a gas flow communication from at least one gas input opening 38 to the connection valve 70 and a fourth port 82 is for providing a gas flow communication from the connection valve 70 typically through interface outlet 36 and along the fresh gas line 7 to the breathing circuit 3 for subject breathing.

FIG. 3 represents a situation where the connection valve 70 is in the first operational state. The single valve member 67 of the connection valve is set to disconnect the apparatus 6 from the gas circuitry of the anesthesia system. In this state the gas flows directly from the first port 79 to the fourth port 82. The connection valve 70 of the interface device 19 may comprise a valve spring 68 forcing the valve member typically automatically to the position where the connection valve is in this first operational state when the actuator 63 of the apparatus 6 does not force the valve member 67 to alternate position. With the actuator 63 the apparatus 6 is able to move the valve member 67 to alternate position, where the connection valve is the second operational state, as presented on FIG. 4 by inducing movement to the communication member 66. On this position the gas from the first port 79 of the interface device 19 is guided through the second port 80 to the at least one gas output opening 39 and further to apparatus 6 through the inlet port 42 and back to the interface device 19 through apparatus outlet port 43 and the gas input opening 38 of the interface device. From the gas input opening the gas flows through the third port 81 guiding the gas flow further towards the patient through the fourth port 82 in the socket of the interface device 19. The first port 79 of the socket on upstream end of the interface device 19 may be in direct flow communication with the gas line 34 and the fourth port 82 of the downstream end of the interface device 19 may be in direct flow communication with the fresh gas line 7. The fourth port 82 of upstream socket communicates with the first port 79 of downstream socket in the first operational state.

As explained hereinbefore the connection valve 70 may comprise the valve member 67, such as a stem, and the valve spring 68 that forces the valve member to default position, but also it may comprise seals 72. These all may be assembled in a valve cavity 71, which is in this embodiment a longitudinal cavity, such as a tubular hole integral to the interface device 19. Each seal 72 is positioned into the valve cavity 71 crosswise to the longitudinal axis of the cavity and the seals follow with predetermined distance one after the other along a longitudinal axis of the valve cavity appropriately to provide the opening and closing of the aforementioned flow connections in both positions of the valve member 67. This positioning may be commenced using spacer rings 73 as presented in FIGS. 3 and 4. These spacer rings provide ports letting gas communication through the spacer.

The valve member 67 is advantageously circular stem or rod of variable thickness along its axis. The valve member, having a longitudinal axis parallel with its movement along the longitudinal axis of the valve cavity 71, may comprise at least three thick sections, which are a first thick section 85, second thick section 86 and third thick section 87. Further it may comprise at least two thin sections along the longitudinal axis of the valve member, which sections are a first thin section 88 and a second thin section 89. The first thin section 88 is between the first thick section 85 and the second thick section 86, while the second thin section 89 is between the second thick section 86 and the third thin section 87. Thus the thick and thin sections may occur alternately one after the other along the longitudinal axis of the valve member 67. Also thin and thick sections are crosswise to the longitudinal axis of the valve member 67.

The thick sections 85, 86, 87 seal against proper seals 72 when the valve member 67 is either in the first position where the connection valve is in the first operational state forced by the valve spring 68 as shown in FIG. 3 or in second position where the connection valve is in the second operational state forced by the actuator 63 as shown in FIG. 4. The first thick section 85 and the second thick section 86 leave therebetween a first cavity 90 partially bordering to the first thin section 88, and similarly the second thick section 86 and the third thick section 87 leave therebetween a second cavity 91 partially bordering to the second thin section 89, which first and second cavities are parts of the valve cavity 71.

In the first operational state the first cavity bordering the first thin section 88 allows gas flow in the first cavity 90 from the first port 79 to the fourth port 82, when proper seals 72 are pressed towards the first thick section 85 and the second thick section 86 preventing or disconnecting the flow between the first port 79 and the second port 80 and advantageously also disconnecting the flow between the third port 81 and the fourth port 82. In the second operational state the first cavity 90 bordering the first thin section 88 allows gas flow through the first cavity 90 providing flow communication between the first port 79 and the second port 80, but the second cavity 91 bordering at least partly the second thin section 89 allows gas flow through a second cavity 91 providing flow communication between the third port 81 and the fourth port 82. The valve member movement to the direction forced by the valve spring 68 is limited with valve cap 74 having an opening for the connection valve interface 40 that the actuator mates when moving the valve member 67. FIGS. 3 and 4 presents four seals 72 as minimum configuration. In the configuration shown in FIG. 4, wherein the valve spring is in a forced position, the apparatus is connected to socket and vents out gas from apparatus outlet port 43 to the gas input opening 38 and through the third port 81 and the fourth port 82 of the interface device 19 towards patient breathing. In FIGS. 3 and 4 there is no extra valve to connect/disconnect the flow from the apparatus 6 to the gas input opening 38 of the interface device, but such valve can be provided if required, especially in case the connection valve 70 is not able to disconnect the flow between the third port 81 and the fourth port 82, in which case the connection valve 70 is only connecting/disconnecting the flow between the first port 79 and the second port 80.

At the first operational state the gas connection from the third port 81 may be open to ambient through the leakage between the third thick section 87 and the valve cap 74 as presented on FIG. 3. If desired, this leak can be sealed with a further seal 72 (not shown) and the space between this further seal and the presented seal next to valve cap can have a further opening. This further opening can be connected to anesthesia system gas scavenging to allow ventilation out of any remainder anesthetics from the channels when vaporizer valve is inactivated.

For the apparatus logic circuit 49 it may be beneficial for proper functionality to have means to identify the position of the communication member 66. Such functionality may be needed e.g. to recognize failure to induce movement of the communication member 66 between the first operational position and the second operational position. The position may be identified with a position sensor 75. Such sensor may be optical, mechanical, or even electrical measuring the actuator current and drawing conclusion from that of the communication member movement.

In accordance with the embodiments shown hereinbefore the connection valve 70 of the apparatus 6 for supplying anesthetic agent is positioned on anesthesia system 1 outside the apparatus 6 for supplying anesthetic agent. This allows disconnection of the apparatus from the anesthesia system and also connection of the apparatus to the anesthesia system. In the embodiment the connection valve 70 is positioned on single axis of single valve member 67. This enables actuation of both the fresh gas flow from the interface device 19 to the apparatus 6 and from the apparatus to the interface device at the same time with single component movement. The valve member 67 defaults with spring-induced bias force to a position where the apparatus is disconnected from the anesthesia system pneumatic circuitry. Having both the inlet- and the outlet valve on same axis prevents the risk of fresh gas occlusion. Unifying two valves on single moving valve member 67 enables to have a single actuator 63 in the apparatus 6 with single communication member 66. This eliminates also risk of fresh gas occlusion due to failing actuator.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

I claim:

1. An interface device for supplying a gas flow for subject breathing, said device comprising:
   at least one socket for detachably connecting an apparatus for supplying anesthetic agent;
   at least one gas output opening for said at least one socket for delivering fresh gas to said apparatus;
   at least one gas input opening for said at least one socket for receiving from said apparatus the fresh gas mixed with anesthetic agent to supply further for subject breathing; and
   a connection valve for said at least one socket and at least four ports in flow communication with said connection valve, a first port receiving the fresh gas guided to said device, a second port providing a gas flow communication with said at least one gas output opening, a third port providing a gas flow communication with said at least one gas input opening, and a fourth port providing a gas flow communication for subject breathing, said connection valve having a first operational state disconnecting a gas flow communication between said first port and said second port and also providing a gas flow communication between said first port and said fourth port, and a second operational state providing a gas flow communication between said first port and said second port and also providing a gas flow communication between said third port and said fourth port.

2. The interface device of claim 1, wherein said connection valve in said first operational state is further configured to disconnect said gas flow communication between said third port and said fourth port.

3. The interface device of claim 1, wherein said connection valve comprises a single valve member configured to move between at least two positions inside a valve cavity to provide said first operational state and second operational state.

4. The interface device of claim 3, wherein said connection valve also comprises a valve spring configured to force said valve member to one of said at least two positions.

5. The interface device of claim 4, wherein said connection valve also comprises a connection valve interface that may receive and transfer a force to force said valve member to another of said at least two positions.

6. The interface device of claim 5, wherein said connection valve interface is in operational contact with said apparatus, wherein the apparatus is configured to force said valve member to said another of said at least two positions when the apparatus is connected to said at least one socket.

7. The interface device of claim 5, wherein said valve spring is in forced position when the apparatus is connected to said at least one socket, whereby said valve member is in said another of said at least two positions.

8. The interface device of claim 3, wherein said connection valve also comprises seals positioned to border said valve cavity, said seals being crosswise to a longitudinal axis of said valve cavity, and said seals being at predetermined distance one after the other along the longitudinal axis of said valve cavity.

9. The interface device of claim 8, wherein said longitudinal axis of said valve member is parallel to said valve cavity, and that said valve member comprises at least three thick sections and at least two thin sections crosswise to said longitudinal axis and which thick and thin sections are configured to occur alternately along the longitudinal axis of said valve member.

10. The interface device of claim 9, wherein said thick sections leaving therebetween thin sections are configured to border at least partly a first cavity and a second cavity inside said valve cavity and which first cavity in the first operational state is configured to connect said first port and said fourth port disconnecting the gas flow to said second port.

11. The interface device of claim 10, wherein said second cavity in the first operational state is configured to disconnect said third port and said fourth port.

12. The interface device of claim 9, wherein said thick sections leaving therebetween thin sections are configured to border at least partly a first cavity and a second cavity inside said valve cavity and which first cavity in the second operational state is configured to connect said first port and said second port.

13. The interface device of claim 12, wherein said second cavity in the second operational state is configured to connect said third port and said fourth port.

14. The interface device of claim 1, wherein said connection valve in said first operational state is configured to connect the gas flow communication between said first port and said fourth port.

15. A method for supplying the gas flow from an interface device
   for subject breathing, said method comprising:
   connecting detachably an apparatus for supplying anesthetic agent to at least one socket of said interface device;
   delivering a fresh gas through at least one gas output opening of said at least one socket to said apparatus;
   receiving through at least one input opening of said at least one socket from said apparatus the fresh gas mixed with anesthetic agent to provide further for subject breathing; and providing gas flow communication in said interface device between a connection valve and at least four ports, a first port receiving the fresh gas guided to said device, a second port providing a gas flow communication with said at least one gas output opening, a third port providing a gas flow communication with said at least one gas input opening, and a fourth port providing a gas flow communication for subject breathing, said connection valve having a first operational state disconnecting a gas flow communication between said first port and said second port and also providing a gas flow communication between said first port and said fourth port, and a second operational state providing a gas flow communication between said first port and said second port and also providing a gas flow communication between said third port and said fourth port.

16. The method of claim 15 further comprising disconnecting in said first operational state said gas flow communication between said third port and said fourth port.

\* \* \* \* \*